United States Patent [19]

Shlain et al.

[11] Patent Number: 5,460,629
[45] Date of Patent: Oct. 24, 1995

[54] ELECTROSURGICAL DEVICE AND METHOD

[75] Inventors: Leonard M. Shlain, Mill Valley; Paul Lubock, Laguna Niguel; Wayne A. Noda, Mission Viejo, all of Calif.

[73] Assignee: Advanced Surgical, Inc., Princeton, N.J.

[21] Appl. No.: 221,975

[22] Filed: Apr. 1, 1994

Related U.S. Application Data

[63] Continuation of Ser. No. 692,809, Apr. 25, 1991, abandoned, which is a continuation-in-part of Ser. No. 652,145, Feb. 6, 1991, abandoned.

[51] Int. Cl.[6] .................................................. A61B 17/39
[52] U.S. Cl. ......................... 606/46; 606/48; 606/49; 606/50
[58] Field of Search ......................... 606/45, 46, 48–52

[56] References Cited

U.S. PATENT DOCUMENTS

| | | |
|---|---|---|
| 1,683,708 | 9/1928 | Wappler et al. . |
| 1,731,069 | 10/1929 | Herman . |
| 1,741,461 | 12/1929 | Herman . |
| 1,798,902 | 3/1931 | Raney . |
| 1,881,250 | 10/1932 | Tomlinson . |
| 1,978,495 | 10/1934 | Landau . |
| 4,418,692 | 12/1983 | Guay ......................................... 606/51 |
| 4,919,129 | 4/1990 | Weber, Jr. et al. . |
| 4,985,030 | 1/1991 | Melzer et al. ............................. 606/51 |
| 5,007,908 | 4/1991 | Rydell . |
| 5,190,541 | 3/1993 | Abele et al. ............................... 606/46 |

FOREIGN PATENT DOCUMENTS

| | | |
|---|---|---|
| 2265344 | 11/1975 | France . |
| 2415263 | 10/1975 | Germany ................................. 606/51 |

*Primary Examiner*—Lee S. Cohen
*Attorney, Agent, or Firm*—Burns, Doane, Swecker & Mathis

[57] ABSTRACT

An electrosurgical probe comprises an elongate probe body having a surgical hook at a distal end thereof. A paddle element is reciprocatably mounted within the distal tip of the elongate body so that it can be shifted between an extended position where it covers the hook tip and a retracted position where it leaves the hook tip exposed. The paddle thus can cooperate with the hook in tissue dissection, clean the hook, as well as provide an alternate electrosurgical probe tip for use in electrosurgical procedures.

25 Claims, 6 Drawing Sheets

ELECTROSURGICAL DEVICE AND METHOD

This application is a continuation of application Ser. No. 07/692,809, filed Apr. 25, 1991, now abandoned, which is a continuation-in-part of application Ser. No. 07/652,145 filed on Feb. 6, 1991, now abandoned, the full disclosure of which is incorporated herein by reference.

BACKGROUND OF THE INVENTION

1. Field of the Invention

The present invention relates generally to the structure and use of surgical instruments. More particularly, the present invention relates to an electrosurgical device which combines a hook electrode and a reciprocatable paddle electrode intended for use in least invasive surgical procedures.

Medical treatment modalities which use electrical energy to change the structure or function of tissue or body organs is referred to generally as "electrosurgery." Electrosurgical procedures most often rely on the application of very high frequency currents to excise tissue and/or close small bleeding blood vessels by electrocauterization. Of particular interest to the present invention are monopolar electrosurgical devices where the patient is grounded and the very high frequency electrical current is applied to desired area of tissue or body organ using a specialized electrode. Electrosurgical procedures are particularly advantageous since they reduce bleeding from small blood vessels, facilitating the handling of highly vascularized tissues while minimizing exposure of the patient to shock and pain.

Least invasive surgical (LIS) techniques, such as laparoscopic, endoscopic, and arthroscopic surgery, are generally performed through small incisions using specialized instruments to perform desired surgical procedures. Usually, the instruments are introduced through a tube, such as a cannula, while the physician observes manipulation of the instruments through specialized imaging equipment, such as laparoscopes, endoscopes, and arthroscopes. Such LIS techniques offer significant advantages over conventional "open" surgical procedures. In particular, the LIS techniques are usually less traumatic, require a shorter recovery time, and are less costly than the corresponding conventional surgical techniques.

The combination of LIS and electrosurgical methodologies promises substantial advantages to both the patient and the treating physician. As described above, LIS reduces patient trauma resulting from the surgical incisions necessary to access the area of the body being treated, while the use of electrosurgical techniques reduces the trauma resulting from the interventional procedure itself.

The adaption of electrosurgical instruments for use in LIS, however, can be problematic. In particular, the incorporation of only a single, limited function in the electrosurgical instrument necessitates frequent exchange and replacement of instruments through the cannula. Such exchange can be time consuming and inefficient. Moreover, electrosurgical instruments frequently produce charred tissue which can adhere to the working surface of the instrument. Usually, such adherent debris requires that the instrument be withdrawn through the cannula and cleaned prior to reintroduction and further use. The need to repeatedly perform such cleaning is also inefficient and time consuming.

For these reasons, it would be desirable to provide improved electrosurgical instruments for use in LIS procedures where the instruments are versatile, capable of self-cleaning, and efficient in achieving their intended purpose. It would be particularly desirable to provide electrosurgical instruments capable of combining a wide variety of different electrode surfaces, such as cylinders, cones, spatulas, balls, needles, blades, hooks, loops, and the like, in a single instrument, where the different electrode surfaces are simultaneously connected to a power source in an efficient manner.

2. Description of the Background Art

French Patent Application No. 2 265 344 describes an electrosurgical hook that can be used for gynecological, ear, nose, and throat surgery. U.S. Pat. Nos. 1,798,902; 1,881,250; and 1,978,495, describe electrosurgical instruments including blades which reciprocate within a frame, which instruments are intended primarily for removing tonsils. U.S. Pat. No. 4,919,129, describes an electrocautery instrument having a self-cleaning reciprocatable electrode/blade. Other electrosurgical instruments are described in U.S. Pat. Nos. 1,683,708; 1,731,069; and 1,741,461.

SUMMARY OF THE INVENTION

The present invention is an electrosurgical probe which combines a pair of separate electrode surfaces which can be used alternatively or in combination for performing electrosurgical procedures. The probe is constructed to permit relative reciprocation of the two electrode surfaces so that either surface can be selectively extended relative to the other to permit its use in a laparoscopic or other surgical procedure. Exemplary electrode surfaces include cylinders, cones, spatulas, balls, needles, blades, hooks, loops, and the like.

The electrosurgical probe comprises an outer elongate body having a proximal end, a distal end, and a lumen extending between said ends. An inner elongate member is reciprocatably mounted within the lumen of the body, and both the outer elongate body and the inner elongate member define exposed electrode surfaces near their distal ends. Moreover, portions of both the outer elongate body and the inner elongate member are electrically conductive and may be coupled to a power supply through an electrical conductor located on a handle which is disposed at the proximal ends of both the body and the member. A mechanism, such as a trigger or pull bar, is provided on the handle for reciprocating the body relative to the member so that either electrode surface can be selectively extended. In this way, the electrosurgical probe can be connected to a power source and either of the electrode surfaces can be selectively utilized by simply extending the surface using the reciprocating mechanism on the handle.

An exemplary embodiment of the present invention is an electrosurgical probe which can be used in either a "hook mode" or a "spatula mode," where the respective hook and spatula components are uniquely arranged to provide both enhanced tissue dissection and cauterization as well as the ability to clean the probe in situ, i.e., without removal from the area of the body being treated. These features are particularly advantageous when the probe is used in least invasive surgical (LIS) procedures, such as laparoscopic, endoscopic, and arthroscopic procedures. In a particularly preferred construction, the electrosurgical probe can also provide for irrigation and/or aspiration of the body region being treated.

The exemplary embodiment of the electrosurgical probe comprises an elongate, usually rigid, probe body having a proximal end and a distal end. The elongate body is connected to both a surgical hook and a paddle element (which acts as the "spatula") at its distal end, and the body is electrically conductive so that power may be supplied to both the surgical hook and the paddle element through an electrical connector located near the proximal end of the body. A means is provided for reciprocating the surgical hook and the paddle element relative to each other so that either the hook or the paddle element can be selectively exposed at the distal tip of the elongate probe body. Preferably, the surgical hook will be fixed to the elongate body, and the paddle element will be mounted at the distal end of a shaft which is slidably received in an axial lumen of the elongate body. Other configurations, however, would be possible so long as they allow for selective exposure of both the surgical hook and paddle element as well as allowing for electrical conduction to the hook and paddle.

In a preferred aspect of the present invention, the elongate body of the probe includes an electrically-conductive tubular sleeve having a lumen which slidably receives the shaft carrying the paddle element. The surgical hook is fixedly attached to the forward end of the sleeve, and both the sleeve and the shaft are electrically conductive, typically being composed at least partly of metal. The electrical connector is attached to the proximal end of the shaft, and contact between the shaft and the sleeve assures that the electric power will be fed to both the surgical hook and the paddle element. The outer surface of the sleeve will be covered with an insulating material in order to prevent unintended electrical contact.

While the construction just described provides a monopolar instrument, where the patient's body acts as the second pole to complete the circuit, the present invention is also suitable for bipolar designs, i.e., where the device itself provides a pair of electrodes for electrotherapy. For example, the surgical hook, paddle element, or both, can be formed as laminated structures including at least two metal (electrically conductive) layers separated by an insulating layer. Such metal layers can thus provide the two electrodes necessary for the bipolar design.

In a second preferred aspect of the present invention, the surgical hook includes at least one, and usually two, planar faces. The paddle element includes a planar surface (or two planar surfaces) that is (are) disposed to slide past and cause a shearing action with the planar face(s) of the surgical hook. Such a shearing action enhances the ability of the surgical hook to dissect tissue and other body structures as well as providing an in situ cleaning capability to remove char and other debris which might otherwise collect on the surgical hook during use. In a particularly preferred configuration, the paddle element has a forked construction which provides for a pair of parallel planar surfaces which engage planar faces on opposite sides of the surgical hook.

According to the method of the present invention, the electrosurgical probe is introduced into an internal body location through an access tube, such as a cannula. One of the electrode surfaces, for example, the surgical hook or the paddle element, on the probe is then selectively engaged against tissue or other body structure, while current is applied to effect dissection or cauterization. The method further comprises selectively retracting the extended electrode surface to expose the other electrode surface when it is desired to use said other surface in an electrosurgical procedure. In this way, the treating physician has ready access to two different electrosurgical capabilities without the need to exchange instruments, for example, by removing a first instrument from a cannula and reconnecting a new instrument to the power source and inserting the new instrument back into the cannula. The method of the present invention further comprises cleaning of the electrode surfaces by relative reciprocation of one surface past the other. This is a particular advantage with the hook and spatula embodiment where cleaning may be accomplished by reciprocating the paddle element past the planar face(s) of the hook. Preferred use of the electrosurgical method is for dissecting the cystic duct from its surrounding or enclosing tissue and the gallbladder from its attachment to the liver.

DESCRIPTION OF THE SPECIFIC EMBODIMENTS

The device and method of the present invention are useful for performing a variety of electrosurgical procedures in both conventional open surgery and least invasive surgery. The present invention will find its greatest use in the performance of laparoscopic, arthroscopic, and endoscopic surgery, where the electrosurgical probe is introduced and manipulated through relatively narrow cannulas, typically having diameters of five millimeters or less.

Particular electrosurgical procedures that may be performed include both tissue dissection and tissue cauterization, where the dissected tissue will usually be subject to simultaneous cauterization. The electrosurgical probe will also be useful for cauterizing small blood vessels in highly vascularized tissue which has been severed or otherwise damaged through the use of other surgical devices.

The electrosurgical probe of the present invention comprises an elongate probe body having proximal and distal ends. The elongate body will usually have a circular cross-section, more usually comprising a cylindrical sleeve and a separate shaft slidably received in an axial lumen of the sleeve. The dimensions of the elongate body are not critical, but the diameter will usually be sufficiently small to allow for passage through a conventional cannula, usually being five millimeters or less in diameter. The elongate body will be sufficiently long to permit access by the distal tip to any desired location in the body, typically having a length in the range from about 25 centimeters to 38 centimeters.

The elongate probe body (including both the sleeve and shaft) will usually be formed from an electrically conductive material, more usually being formed from a metal such as surgical stainless steel, or the like. Other materials, such as electrically conductive polymers might also find use, and it would further be possible to form composite structures where only a portion of the elongate probe body would be electrically conductive.

An inner elongate member will be reciprocatably mounted within the outer elongate body with at least a portion of its distal end being electrically conductive. The electrode surfaces will be defined at the distal ends of the elongate body and the inner elongate member, respectively, so that relative reciprocation of the body and the member can provide for selective exposure of either of the electrode surfaces. The distal portions of the elongate body and the inner elongate member will be electrically coupled, typically by direct sliding contact therebetween, at their distal ends. In this way, electrical connection of either the distal end of the body or by distal end of the inner elongate member will provide for the electrical connection of both electrode surfaces simultaneously. Typically, the inner elongate member will be electrically conductive along its entire length and will be coupled at its proximal end to an electrical power supply. Alternatively, the outer elongate body can be electrically conductive along its entire length and connected to the power supply, or both the elongate body and the inner elongate member can be electrically conductive along their entire lengths.

In a first exemplary embodiment of the present invention, an electrically conductive surgical hook and an electrically conductive paddle element are disposed on the distal end of the elongate probe body. The hook and paddle element are mounted so that they are free to reciprocate relative to each other so that either the hook or the paddle element may be selectively exposed at the distal tip of the elongate probe body. In a specific embodiment, the hook is mounted on the sleeve while the paddle element is mounted on the shaft. A means for reciprocating the shaft relative to the sleeve, such as a thumb lever attached to the shaft, allows the user to selectively extend the paddle element past the hook.

The surgical hook and the paddle element will usually be formed from a metal, such as surgical stainless steel, and will be electrically coupled to the elongate probe body, typically being physically attached to the sleeve and the shaft, respectively, so that current may be passed directly therethrough. The exterior of the sleeve will typically be covered with an insulating polymeric or plastic layer, such as polyolefin, to prevent unintentional contact and shorting of the probe body during use.

One or more ports or other fluid connectors will optionally be provided on the elongate probe body to permit irrigation and/or aspiration of the fluids or smoke through the probe tip. Conveniently, a port may be formed near the proximal end of the shaft and the shaft may be hollowed (or otherwise provided with an axial lumen) to permit fluid transfer between the distal tip and the port. In this way, the electrosurgical probe may be connected to external sources of fluid and/or vacuum.

A wide variety of other electrode surfaces may be provided on the electrosurgical probe of the present invention, typically being provided in pairs at the distal ends of the outer elongate body and the inner elongate member, respectively. In addition to the hook and spatula just described, suitable electrode surfaces include cylinders, cones, balls, needles, blades, loops, and the like. It will generally be possible to place any of these electrode surfaces on either the outer elongate body or the inner elongate member. Specific instructions are exemplified hereinafter in the drawings.

An electrical connector will also be provided on the device to permit attachment to a conventional electrosurgical power system. Conveniently, a 3/32 inch diameter plug connector will be attached to either the sleeve or the shaft, with contact between the sleeve and shaft assuring that current will flow through both. Suitable power supplies are available from vendors, such as Valleylab, Inc. (a Pfizer company), Boulder Colo.; Aspen Labs, Inc. (a Conmed company), Englewood, Colo.; Birtcher Corp., Irvine, Calif.; and Bard Electro Medical Systems, Inc., Englewood, Colo.

An insulating cover will be formed over at least part of the elongate probe body, usually being formed as a handle attached over the proximal end of the probe body. The handle will usually have a larger diameter than the remaining length of the elongate probe body to facilitate manual handling. Conveniently, the fluid connector(s), electrical connector, thumb lever, and other features of the device may be formed on or through the handle to provide for convenient access during use.

Figures 1, 2, 3:
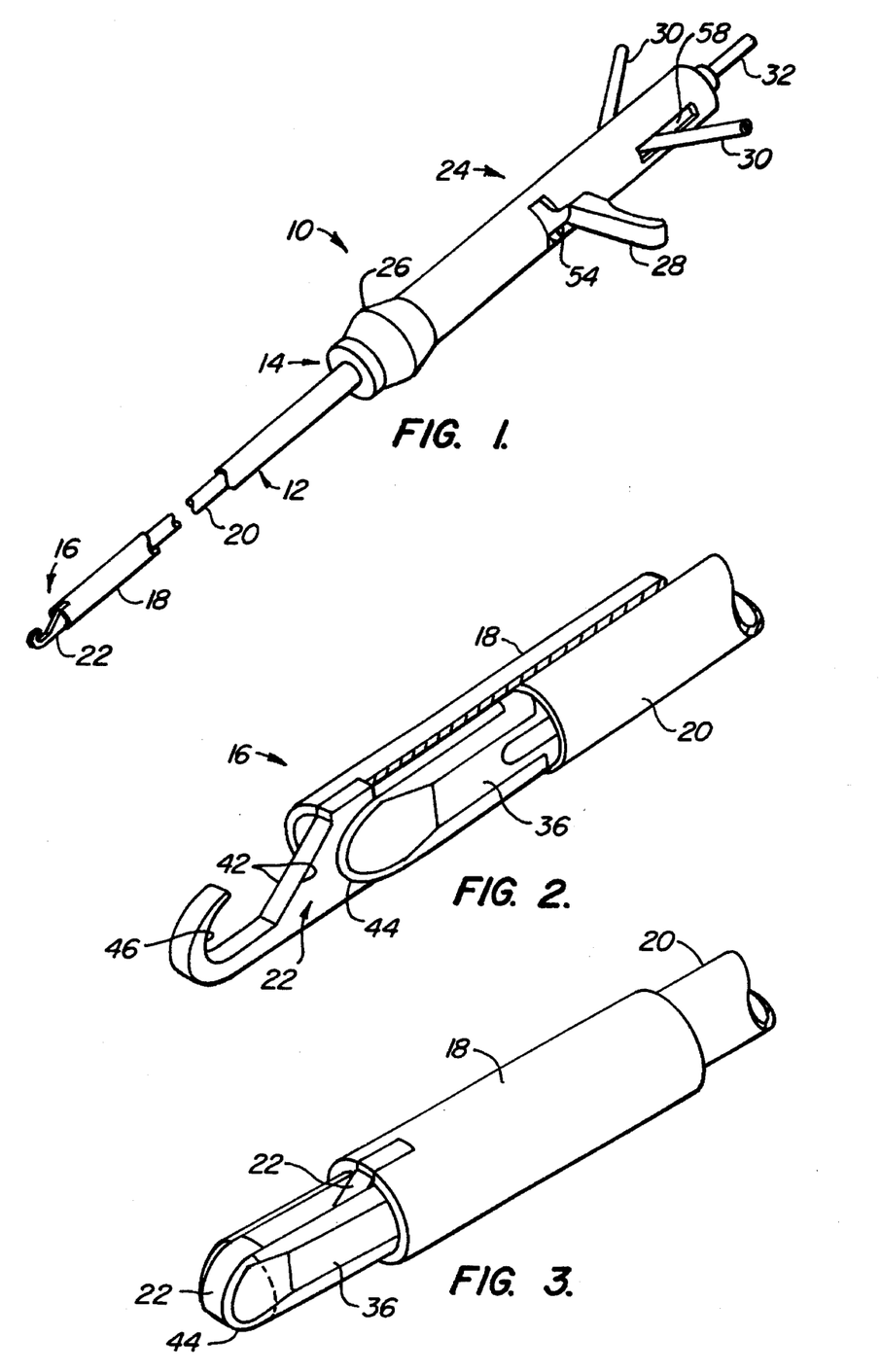
FIG. 1 is a perspective view of an electrosurgical probe constructed in accordance with the principles of the present invention.
FIG. 2 is a detailed view of the distal end of the electrosurgical probe of FIG. 1, with portions broken away, shown with its paddle element in a retracted configuration.
FIG. 3 is a detailed view of the distal end of the electrosurgical probe of FIG. 1, shown with the paddle element in its extended configuration.

Referring now to the figures, the construction of a surgical probe 10 which is exemplary of the present invention will be described. Referring in particular to FIG. 1, the electrosurgical probe 10 includes an elongate probe body 12 having a proximal end 14 and distal end 16. The elongate body 12 includes both an outer sleeve 18 and an inner shaft 20 slidably received in an axial lumen of the sleeve. A surgical hook 22 is secured to the distal end 16 of the elongate body 12, more specifically being secured to the sleeve 18. A handle 24 is attached to the proximal end 14 of the elongate body 12 and covers at least a portion thereof. The handle 24 may be formed from an electrically insulating material, such as acrylonitrile-butadiene-styrene (ABS), polycarbonate, Delrin® (an acetal resin), and the like. An enlarged region 26 may be formed in the distal end of the handle to facilitate manipulation, and a thumb lever 28 (for reciprocating the paddle element as described in more detail hereinafter), fluid connectors 30, and an electrical connector 32 will conveniently be located within the handle.

Figure 4:
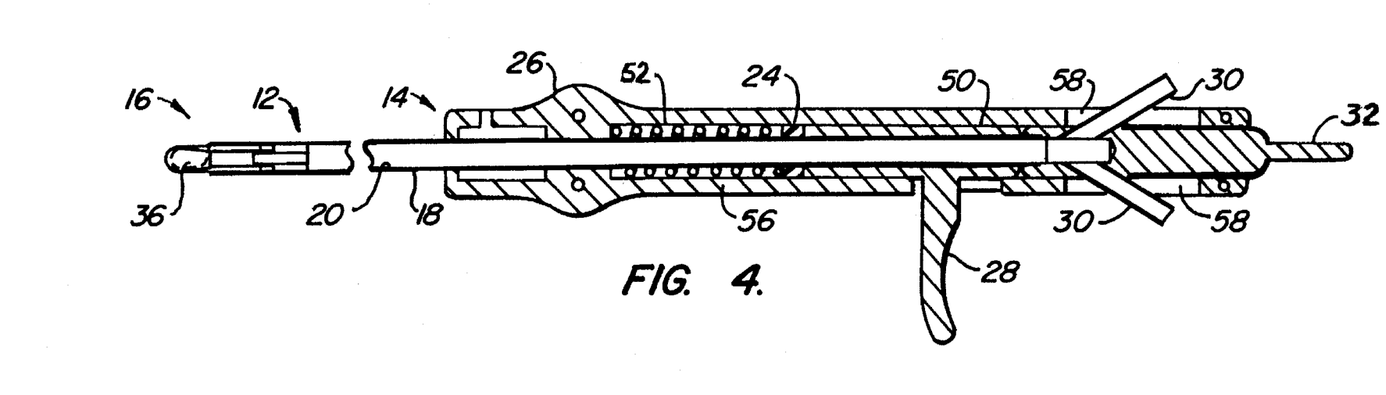
FIG. 4 is a cross sectional view of the electrosurgical probe of FIG. 1.
Figures 5, 7:
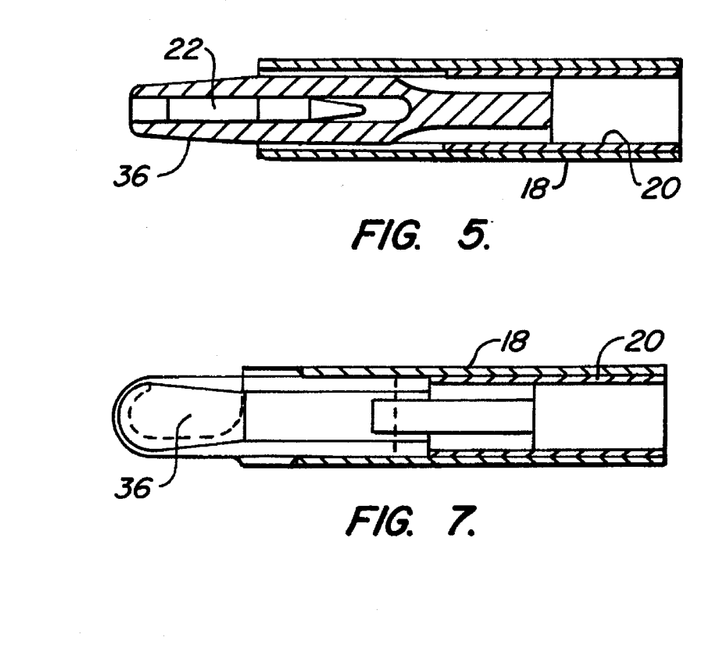
FIGS. 5 and 6 are top plan views of the distal end of the electrosurgical probe, shown in cross-section, with the paddle element illustrated in the extended and retracted configurations, respectively.
FIGS. 7 and 8 are side elevational views of the distal end of the electrosurgical probe, shown in cross-section, with the paddle element illustrated in the extended and retracted configurations, respectively.
Figure 6:
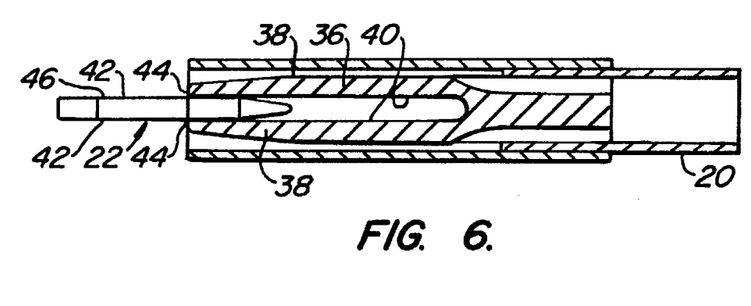
Figure 8:
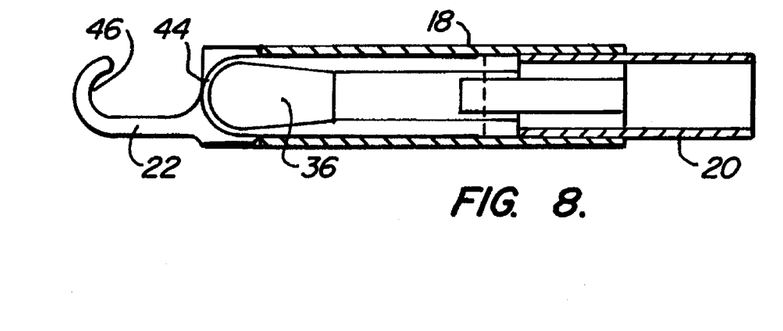

Referring now to FIGS. 2–8, the internal construction of the electrosurgical probe 10 will be described. A paddle element 36 is secured to the distal end of slidable shaft 20. The paddle element 36 has a forked configuration including a pair of individual plates 38 defining flat surfaces 40 which are disposed to slide against flat faces 42 formed on either side of the surgical hook 22. In this way, the paddle 36 may be shifted between an extended configuration, as illustrated in FIGS. 3, 5, and 7, and a retracted configuration, as illustrated in FIGS. 2, 6, and 8.

Axial translation of the paddle element 36 past the surgical hook 22 has several advantages as described above. First, a leading edge 44 of each of the plates 38 will cooperate with inner edges 46 of the hook 22 to provide a shearing action as the paddle element is moved forward. Thus, when tissue or other body structure is held within the hook 22, the shearing action of the paddle 36 may enhance the dissection afforded by the electric current. Additionally, the motion of the paddle 36 past the surgical hook 22 will be able to clean char and other debris from the hook which may adhere to the hook during use.

Referring now in particular to FIG. 4, the thumb lever 28 is connected to a shuttle cylinder 50 which is slidably received within an interior chamber 52 within the handle 24. The shuttle cylinder 50 is attached to the exterior of shaft 20 so that the lever 28 may be used to move to reciprocate shaft 20 back and forth in the axial direction. In this way, the paddle element 36 may be extended and retracted within the distal end of sleeve 18, as described above. The lever 28 is received in a T-shaped slot 54 in the handle so that the lever may be locked in its forward position by rotating the thumb lever 28 into either of the lateral portions of the slot. A spring 56 is provided to return the lever 28 (and thus the shaft 20) back to its proximal position when the handle is moved out of the lateral slot extension.

Conveniently, the shaft 20 is hollow and the fluid connectors 30 are formed as lateral branches from the shaft near the proximal end. The lateral branches are preferably angled back (i.e., proximally) and extend through slots 58 formed in the handle 24 to permit movement of the shaft in the axial direction. The open proximal end of the shaft 18 is sealed by the electrical connector 32 which extends out through the open proximal end of handle 24.

The distal end of shaft 18 is attached to the paddle element 36, as described above. The paddle element 36, however, does not seal the distal end of shaft 20 so that fluid introduced through the connector 30 may flow down the central lumen of shaft 20 and out past the paddle element. Similarly, fluid or smoke may be aspirated in through the distal end of shaft 20 by applying a vacuum on either of the connectors 30 in a conventional manner.

The electrosurgical probe as just described will typically be provided in a sterile package and will be intended for a single use only, although it may be possible to provide sterilizable and reusable devices. After removing the probe 10 from its packaging, the probe may be connected to a conventional electrosurgical power supply through connector 32. The irrigation and/or aspiration sources will be connected through connectors 30, and the patient should be properly grounded in accordance with the electrosurgical power system manufacturer's instructions.

The electrosurgical probe may then be introduced through a cannula or other access tube to a region of interest having tissue or other body structures requiring electrosurgical treatment. The distal end of the probe may be guided under standard visualization techniques, such as laparoscopic, endoscopic, or arthroscopic systems. The distal probe tip may be converted from the hook configuration to the spatula configuration by depressing the thumb lever 28 distally against the tension of spring 56. The paddle element 36 may be locked into place by twisting the lever 28 so that it enters either of the lateral portions of slot 54. The paddle tip can be converted back to the hook tip by unlocking the thumb lever 28. Depressing the thumb lever 28 also serves to remove debris from the sides of the hook tip 22. The electrosurgical probe 10 is particularly suitable for removing tissue surrounding the cystic duct and dissecting the gallbladder from the liver bed in laparoscopic gallbladder removal. Optionally, the paddle element 36 may be extended distally, as described above, to enhance shearing of tissue surrounding the gallbladder as well as aiding in coaggulating bleeding sites in the liver bed. The paddle 36 may also be used to clean the hook tip 22 during and after the procedure.

Figure 9:
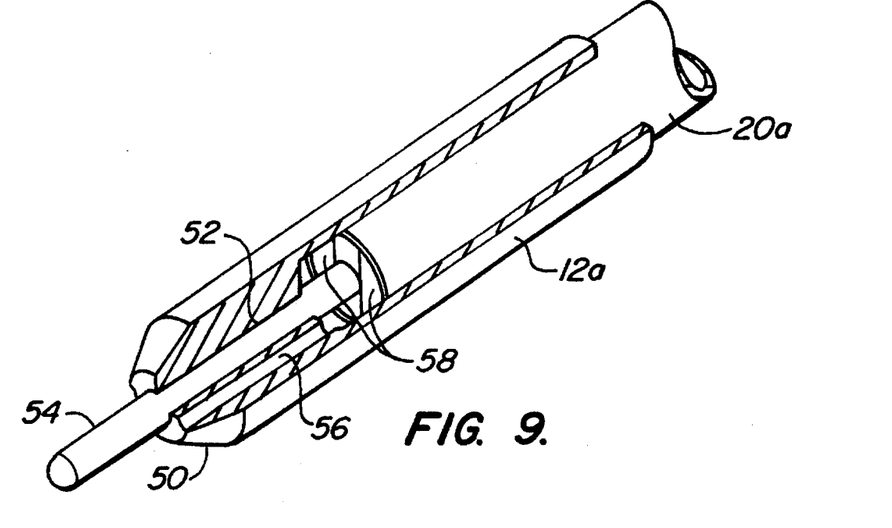
FIG. 9 illustrates an alternate configuration of the electrosurgical probe of the present invention where a first electrode surface is a cone and a second electrode surface is a needle.

The distal end of electrosurgical probe 10 can be modified to carry a variety of other electrode surfaces in addition to the hook 22 and spatula 36, as just described. Referring to FIG. 9, the distal end of elongate probe body 12a can be modified into a cone 50 having an axial shaft 52 which is adapted to receive needle 54 which is secured to the distal end of inner elongate member or shaft 20a. The inner elongate member 20a can be reciprocated relative to the outer probe body 12a in the manner just discussed for electrosurgical probe 10. Thus, the treating physician will be able to use the needle 54 when it is extended or use the cone electrode 50 when the needle is retracted.

The electrosurgical probe illustrated in FIG. 9 further includes one or more axial lumens 56 through the distal end of the body 12a in order to permit perfusion and aspiration of the region being treated. In this regard, the inner member 20a retains openings 58 in its distal end to permit communication with the fluid connectors 30 (FIG. 4) which are present on its proximal end.

Figure 10A:
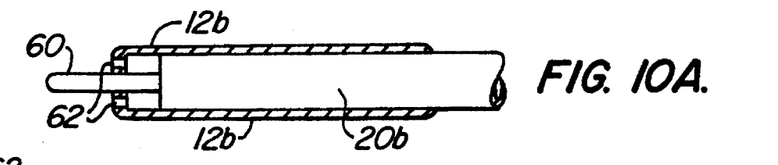
FIGS. 10A–10C illustrate another alternate embodiment of the electrosurgical probe of the present invention where the electrode surfaces are a cylinder and needle, respectively.
Figure 10B:
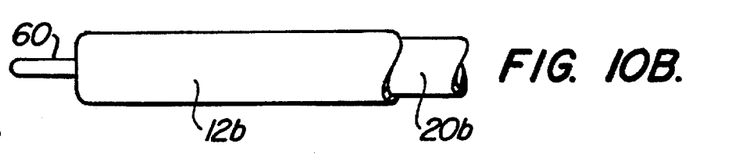
Figure 10C:
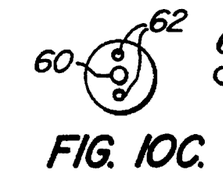

The combination of a cylindrical electrode surface and a needle electrode is illustrated in FIGS. 10A–10C. A needle 60 is secured to the distal end of inner member 20b while the probe body 12b is formed into the desired cylinder at its distal end. Perfusion/aspiration ports 62 are provided in the distal end of the probe body 12b.

Figure 11A:
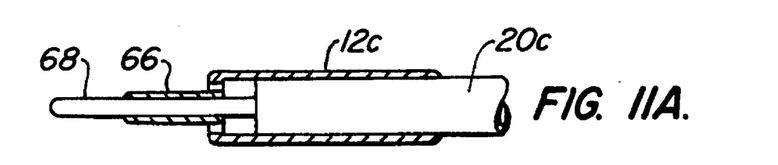
FIGS. 11A–11C illustrate yet another alternate embodiment of the electrosurgical probe of the present invention where the electrode surfaces are a spatula and needle, respectively.
Figure 11B:
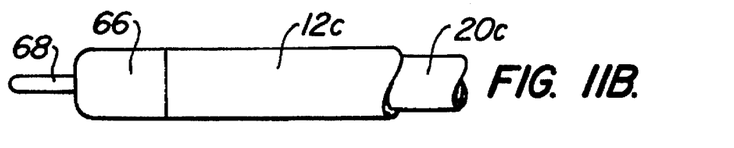
Figure 11C:
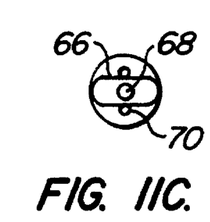

A combination of a spatula electrode 66 and a needle electrode 68 is illustrated in FIGS. 11A–11C. The spatula 66 is secured to the distal end of probe body 12c while the needle 68 is secured to the distal end of inner elongate member 20c. Perfusion ports 70 are provided in the distal end of the probe body 12C.

Figure 12A:
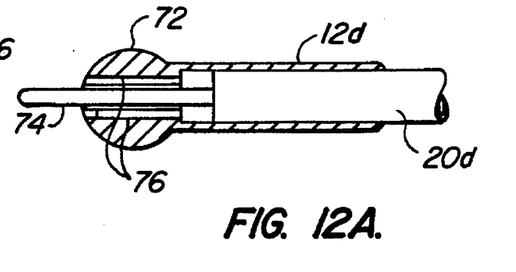
FIGS. 12A–12D illustrate yet another alternate embodiment of the electrosurgical probe of the present invention where the electrode surfaces are a ball and needle, respectively.
Figure 12B:
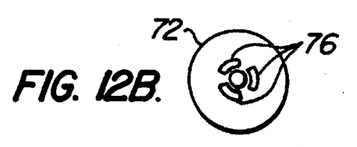
Figure 12C:
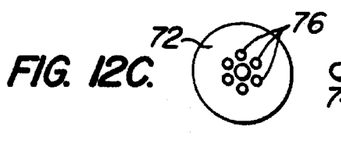
Figure 12D:
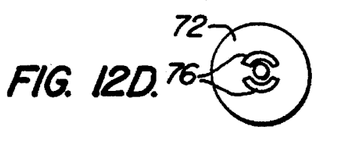

The combination of a ball electrode 72 formed at the distal end of probe body 12d and needle electrode 74 formed at the distal end of the inner elongate member 20d is illustrated in FIGS. 12A–12D. The ball electrode 72 will include perfusion/aspiration lumens 76 which may take a variety of configurations as illustrated in FIGS. 12B–12D, respectively.

Figure 13A:
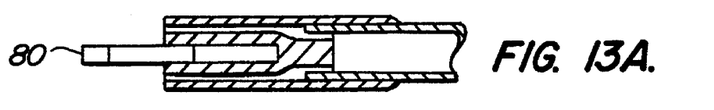
FIGS. 13A–13C and 14A–14C illustrate two additional alternate embodiments of the electrosurgical probe of the present invention where the electrode surfaces are a hook and a spatula, respectively.
Figure 13B:
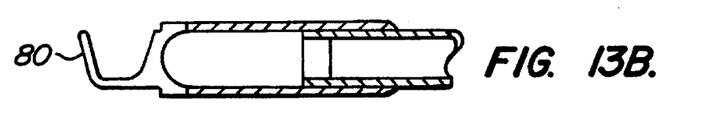
Figure 13C:
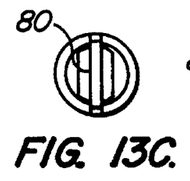
Figure 14A:
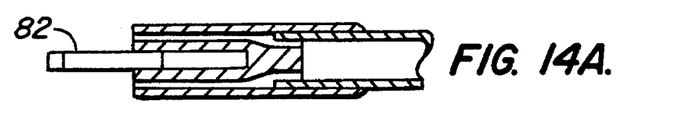
Figure 14B:
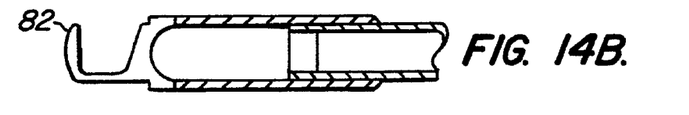
Figure 14C:
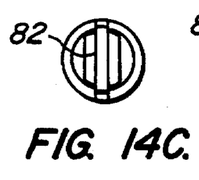

Alternate designs for a hook and spatula electrosurgical probe are set forth in FIGS. 13A–13C and 14A–14C. In FIGS. 13A–13C, hook 80 has a relatively open configuration relative to the hook 22 of FIGS. 1–8. Hook 82 in FIGS. 14A–14C has an intermediate configuration between hooks 80 and 82.

Figure 15A:
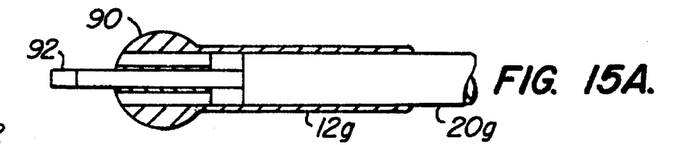
FIGS. 15A–15C and 16A–16C illustrate two more alternate embodiments of the electrosurgical probe of the present invention where the electrode surfaces are a ball and a hook, respectively.
Figure 15B:
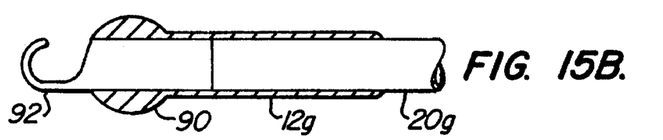
Figure 15C:
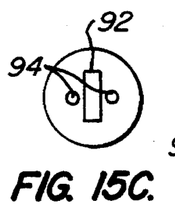

Referring now to FIGS. 15A–15C, a ball electrode 90 is formed at the distal end of probe body 12g and a hook electrode 92 is formed on the distal end of elongate inner member 20g. Axial perfusion/aspiration lumens 94 are formed through the ball 90.

Figure 16A:
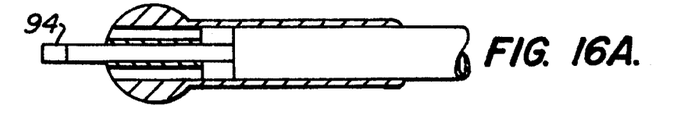
Figure 16B:
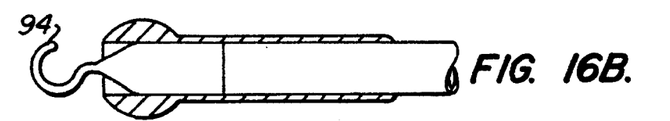
Figure 16C:
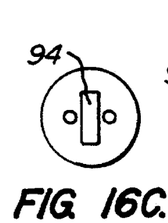

FIGS. 16A–16C illustrate a ball and hook electrosurgical probe configuration similar to that of FIGS. 15A–15C, except that the hook 94 has a different configuration.

Figure 17A:
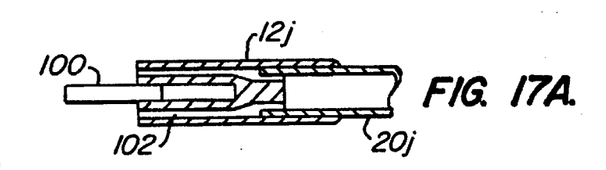
FIGS. 17A–17C and 18A–18C illustrate yet two more embodiments of the electrosurgical probe of the present invention where the electrode surfaces are a loop and a spatula, respectively.
Figure 17B:
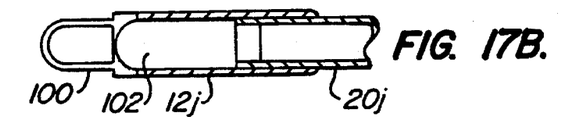

FIGS. 17A–17B illustrate a probe having a loop 100 formed at the distal end of probe body 12j and a spatula 102 formed at the distal end of inner elongate member 20j. Perfusion and aspiration may be effected through the open end of the probe body 12j.

Figure 17C:
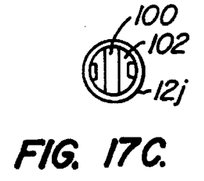
Figure 18A:
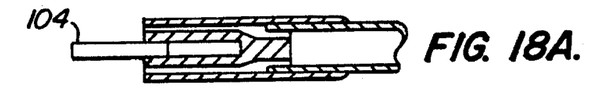
Figures 18B, 18C:
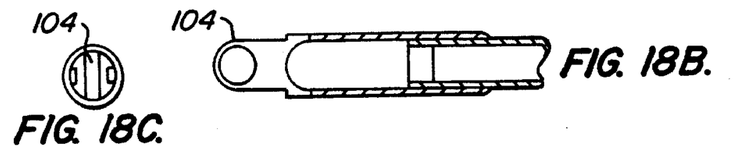

FIGS. 18A–18C illustrate a loop 104 and spatula 102 electrosurgical probe which is generally similar to that illustrated in FIGS. 17A–17C, except the loop 104 has a different configuration.

Figures 19A, 19B, 19C:
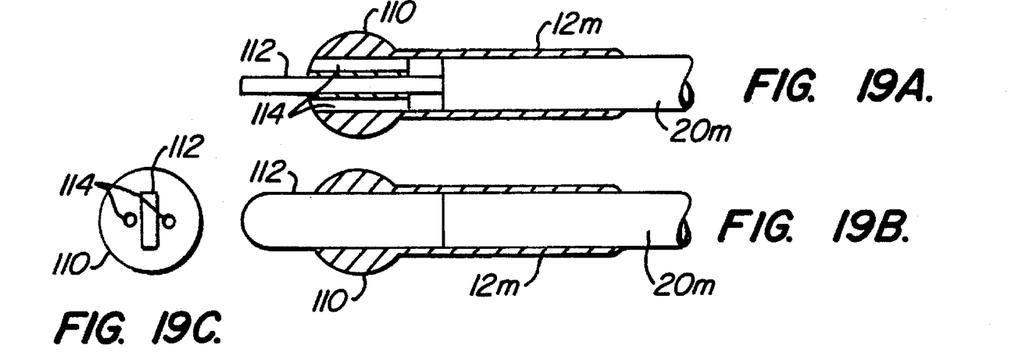
FIGS. 19A–19C illustrate an additional embodiment of the electrosurgical probe of the present invention where the electrode surfaces are a ball and a spatula, respectively.

FIGS. 19A–19C illustrate an electrosurgical probe having a ball electrode 110 formed at the distal end of probe body 12m and a spatula electrode 112 formed at the distal end of inner elongate member 20m. Axial perfusion/aspiration lumens 114 are formed through the ball electrode 110.

Figures 20A, 20B, 20C:
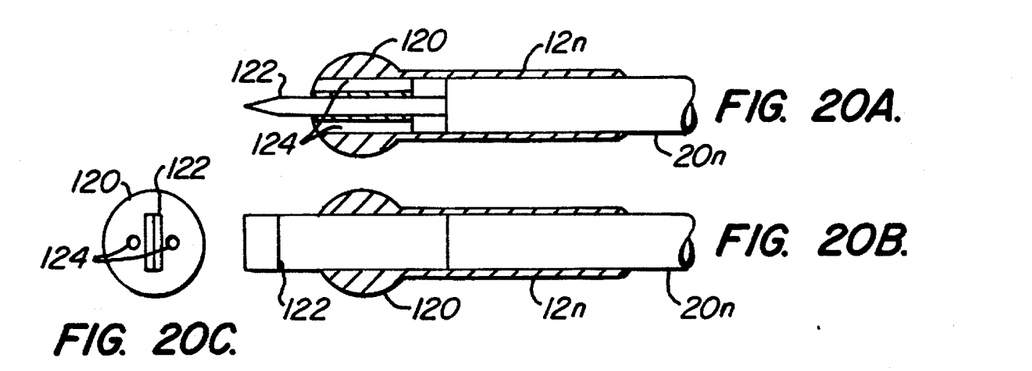
FIGS. 20A–20C illustrate a further alternate embodiment of the electrosurgical probe of the present invention where the electrode surfaces are a ball and a blade, respectively.

FIGS. 20A–20C illustrate an electrosurgical probe having a ball electrode 120 formed at the distal end of probe body 12n and a blade electrode 122 formed at the distal end of inner elongate member 20. Axial perfusion/aspiration lumens 124 are formed through the ball electrode 120.

Figure 21A:
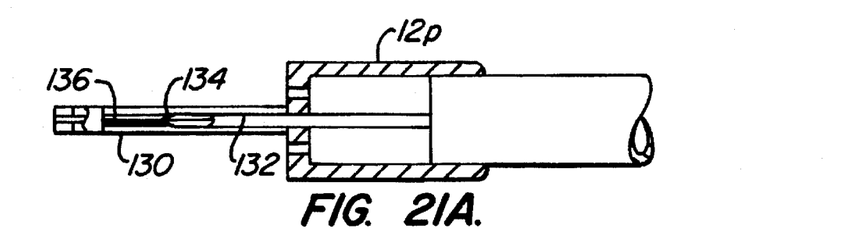
FIGS. 21A–21B illustrate yet a further embodiment of the electrosurgical probe of the present invention, where the electrode surfaces are a hook and blades which are disposed in a nested configuration.
Figure 21B:
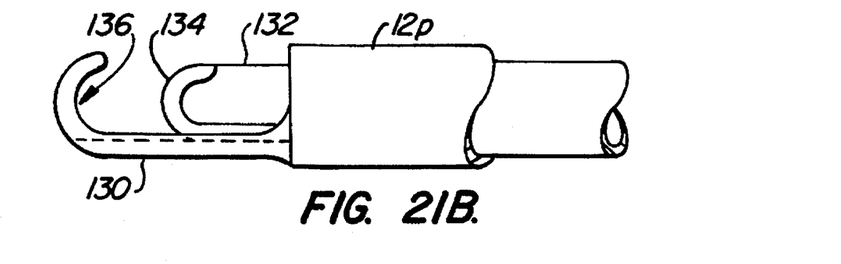

Referring lastly to FIGS. 21A and 21B, an electrosurgical probe having a hook electrode 130 formed at the distal end of probe body 120 is illustrated. A blade electrode 132 is formed at the distal end of inner elongate member 20p, and the hook 130 and blade 132 are disposed so that a sharpened leading edge 134 of the blade nests into and mates with a groove 136 formed along the inner edge of the hook electrode 130. In this way, the blade 132 can be advanced to provide a cutting action as it is brought up against the hook 130. It will be appreciated that the blade 132 could alternately be in the form of a second hook.

Although the foregoing invention has been described in detail for purposes of clarity of understanding, it will be obvious that certain modifications may be practiced within the scope of the appended claims.

What is claimed is:

1. An electrosurgical probe comprising:
    an elongate body having a proximal end and a distal end, wherein said body is electrically conductive along its length;
    a surgical hook electrically coupled to the distal end of the elongate body;
    a paddle element electrically coupled to the distal end of the elongate body;
    means for mounting the surgical hook and paddle element to reciprocate relative to each other, whereby the hook or the paddle element can be exposed and the relative movement can clean adherent debris;
    an electrical connector electrically coupled to hook and paddle element and disposed near the proximal end of the elongate body; and
    an electrically insulating cover on the body near the proximal end.

2. An electrosurgical probe as in claim 1, wherein the elongate body is a metal tube having an insulating layer formed over its exterior.

3. An electrosurgical probe as in claim 1, wherein the surgical hook includes at least one planar face and the paddle element includes at least one planar surface disposed to shear against the planar face of the hook.

4. An electrosurgical probe as in claim 3, wherein the surgical hook includes two planar faces on opposite sides thereof and the paddle element is forked and includes two planar surfaces disposed to shear against the planar faces of the hook.

5. An electrosurgical probe as in claim 1, wherein the surgical hook is fixedly attached to the elongate body and the paddle element is slidably attached to the elongate body.

6. An electrosurgical probe comprising:
    an electrically conductive tubular sleeve having a proximal end, a distal end, and a lumen extending between said proximal and distal ends;
    an electrically conductive surgical hook attached to the distal end of the tubular sleeve;
    a paddle element reciprocatably mounted within the distal end of the lumen and disposed to slide past at least one side of the surgical hook;
    means for reciprocating the paddle element between a retracted position inside the lumen and an extended position which covers the hook;
    an electrical connector electrically coupled to the surgical hook and paddle element and disposed near the proximal end of the tubular sleeve; and
    an electrically insulating cover on the sleeve near its proximal end.

7. An electrosurgical probe as in claim 6, wherein the tubular sleeve is metal having an insulating layer formed over its exterior.

8. An electrosurgical probe as in claim 6, wherein the surgical hook includes at least one planar face and the paddle element includes at least one planar surface disposed to shear against the planar face of the hook.

9. An electrosurgical probe as in claim 8, wherein the surgical hook includes two planar faces on opposite sides thereof and the paddle element is forked and includes two planar surfaces disposed to shear against the planar faces of the hook.

10. An electrosurgical probe as in claim 6, wherein the means for reciprocating includes a shaft slidably received in the lumen of the tubular sleeve and a lever attached to the shaft, wherein the paddle element is attached to a distal end of the shaft and reciprocation is effected using the lever.

11. An electrosurgical probe comprising:
    an electrically conductive tubular sleeve having a proximal end, a distal end, and a lumen extending between said proximal and distal ends;
    an electrically conductive surgical hook attached to the distal end of the tubular sleeve and disposed to project distally from the lumen thereof;
    an electrically conductive shaft having a proximal end and a distal end, and being slidably received in the lumen of the tubular sleeve;
    a paddle element attached to the distal end of the shaft and disposed to slide past the surgical hook;
    means for reciprocating the shaft so that the paddle element may be shifted between a retracted position inside the lumen and an extended position which covers the surgical hook;

an electrical connector electrically coupled to the surgical hook and paddle element and disposed near the proximal end of the shaft; and an electrically insulating cover on the tubular sleeve near the proximal end.

12. An electrosurgical probe as in claim 11, wherein the electrically conductive shaft is hollow and at least one fluid connector is disposed near the proximal end of and in fluid communication with said shaft.

13. An electrosurgical probe as in claim 11, wherein the cover is an elongate handle attached to the proximal end of the tubular sleeve and having a central lumen which is axially aligned with the lumen of said tubular sleeve, and wherein the electrically conductive shaft extends through the lumen in the handle.

14. An electrosurgical probe as in claim 13, wherein the means for reciprocating the shaft includes a lever which projects radially from the shaft and an axially extending slot formed in the handle, whereby the shaft can be reciprocated by axially translating the lever.

15. An electrosurgical probe as in claim 11, wherein the paddle element is forked and includes a pair of surfaces disposed so that one surface will shear against each side of the hook as the paddle element is extended.

16. An electrosurgical method comprising:

introducing an electrosurgical probe to an internal body location through an access tube;

selectively engaging either a first electrode surface or a second electrode surface on the probe against tissue or other body structure; and passing current simultaneously through both electrodes of the probe to effect severing or cauterization by the engaged electrode surface;

wherein the first electrode surface is a paddle, and wherein the method further comprises selectively retracting the paddle within the electrosurgical probe prior to engaging the second electrode surface which is a surgical hook against tissue or other body structure.

17. An electrosurgical method as in claim 16, further comprising selectively extending the paddle past the surgical hook prior to engaging the paddle against tissue or other body structure.

18. An electrosurgical method comprising:

introducing an electrosurgical probe to an internal body location through an access tube;

selectively engaging either a first electrode surface or a second electrode surface on the probe against tissue or other body structure;

passing current simultaneously through both electrodes of the probe to effect severing or cauterization by the engaged electrode surface; and moving the first electrode surface past the second electrode surface to effect a shearing action to clean the electrode surfaces while the probe remains in the internal body location.

19. An electrosurgical probe for use with a power supply, the electrosurgical probe comprising:

an outer elongate body having a proximal end, a distal end, and a lumen extending between said ends, wherein at least a portion of the distal end of the body is electrically conductive and defines an exposed electrode surface;

an inner elongate member reciprocatably mounted in the lumen of the outer elongate body, said inner elongate member having a proximal end and a distal end, wherein at least a portion of the distal end of the member is electrically conductive and defines an exposed electrode surface;

a handle disposed at the proximal ends of the body and member;

means on the handle for reciprocating the body relative to the member; and an electrical connector on the handle which connector is electrically coupled to the electrically conductive portions of both the body and the member for connection to the power supply.

20. An electrosurgical probe as in claim 19, wherein the outer elongate body is electrically conductive along its entire length and attached at its proximal end to the electrical connector, whereby the inner member is electrically coupled by contact with the lumen of the outer body.

21. An electrosurgical probe as in claim 19, wherein the inner elongate member is electrically conductive along its entire length and attached at its proximal end to the electrical connector, whereby the outer body is electrically coupled by contact between its lumen and the inner member.

22. An electrosurgical probe as in claim 19, wherein the distal end of the outer elongate body defines an electrode surface having a shape selected from the group consisting of cylinder, cone, spatula, and ball.

23. An electrosurgical probe as in claim 19, wherein the distal end of the inner elongate member defines an electrode surface having a shape selected from the group consisting of needle, blade hook, spatula, and loop.

24. An electrosurgical probe as in claim 19, wherein the distal end of the outer elongate body defines an electrode in the shape of a hook and the distal end of the inner elongate member defines a sharpened edge which mates with the hook.

25. An electrosurgical probe as in claim 24, wherein the sharpened edge is a flat blade.

* * * * *